United States Patent [19]

Pellerite et al.

[11] Patent Number: 5,274,159
[45] Date of Patent: Dec. 28, 1993

[54] DESTRUCTABLE FLUORINATED ALKOXYSILANE SURFACTANTS AND REPELLENT COATINGS DERIVED THEREFROM

[75] Inventors: Mark J. Pellerite; Richard R. M. Jones, both of Woodbury, Minn.

[73] Assignee: Minnesota Mining and Manufacturing Company, St. Paul, Minn.

[21] Appl. No.: 19,069

[22] Filed: Feb. 18, 1993

[51] Int. Cl.$^5$ .............................. C07F 7/08; C07F 7/10; B32B 9/04
[52] U.S. Cl. .............................. 556/485; 556/400; 556/413; 556/488; 428/411.1; 252/47.5; 252/48.4; 252/DIG. 1; 524/860
[58] Field of Search ............. 556/485, 488, 400, 413, 556/422, 427, 428, 465, 482; 252/DIG. 1, 47.5, 48.4, 54, 58; 526/243, 248; 524/858, 860, 869; 428/391, 411.1, 421

[56] References Cited

U.S. PATENT DOCUMENTS

| | | | |
|---|---|---|---|
| 2,476,307 | 7/1949 | Klein et al. | 260/448.8 |
| 4,597,894 | 7/1986 | Abe et al. | 556/485 X |
| 4,865,910 | 9/1989 | Inoguchi et al. | 428/268 |
| 4,929,666 | 5/1990 | Schmidt et al. | 524/516 |
| 5,006,624 | 4/1991 | Schmidt et al. | 526/243 |
| 5,028,679 | 7/1991 | Terae et al. | 556/485 X |
| 5,068,387 | 11/1991 | Kleyer et al. | 556/485 |

Primary Examiner—Arthur C. Prescott
Attorney, Agent, or Firm—Gary L. Griswold; Walter N. Kirn; Lorraine R. Sherman

[57] ABSTRACT

The present invention provides liquid, destructible fluorinated nonionic surfactants that are water-soluble or dispersible, that are useful as stabilizers for emulsions, and that on curing as a layer on a substrate can provide the substrate with an oil- and water-repellent coating that is free of surfactant, the destructible surfactant comprising a fluorocarbylalkoxysilane having at least one polyfluorinated aliphatic group that is both hydrophobic and oleophobic and at least one, preferably two, polyoxyalkylene or other hydrophilic groups which can be cleaved from the hydrophobe by hydrolysis. More particularly, a fluorocarbylalkoxysilane comprises at least one polyfluorinated aliphatic group and at least one polyoxyalkylene group or other hydrophilic group, said fluorocarbylalkoxysilane being destructible by hydrolysis.

The invention further provides an aqueous composition for providing a substrate with an oil and water repellent coating comprising the fluorocarbylalkoxysilane of the invention as well as a process for providing a substrate with an oil and water repellent coating.

24 Claims, No Drawings

DESTRUCTABLE FLUORINATED ALKOXYSILANE SURFACTANTS AND REPELLENT COATINGS DERIVED THEREFROM

FIELD OF THE INVENTION

This invention relates to reactive nonionic surfactants and to compositions containing the reactive nonionic surfactants. The compositions when coated on a substrate and cured can provide both water and oil repellency to the substrate.

BACKGROUND OF THE INVENTION

Surfactants are well known compounds that are used in many fields for providing low surface tension resulting in increased wettability, spreadability, emulsifiability, dispersibility, penetrability, and improved adhesion.

All surfactants are comprised of a hydrophobic segment, a hydrophilic segment, and a connecting linkage of intermediate polarity joining the two segments together. Surfactants are classified as cationic, anionic, amphoteric, or nonionic depending on whether the hydrophilic segment contains, respectively, a cationic group, an anionic group, both a cationic and an anionic group, or a nonionic hydrophilic group. The nonionic hydrophilic segment, generally, is a polyoxyalkylene group, such as the product of oligomerization of ethylene oxide, but may also be a polyhydroxylated group such as sorbitol or glycerol, their alkyl ether derivatives, or their polyoxyalkylene derivatives. Amine oxide surfactants are also classified as nonionic, having only formal charges in the N—O hydrophile. The hydrophobic segment has generally been a long chain hydrocarbyl group, a polyfluorinated aliphatic group, or a polysiloxane group.

Examples of nonionic surfactants having, for instance, a linear or branched, alkyl or alkylaryl, hydrocarbyl hydrophobic segment and a polyethylene oxide hydrophilic segment where the two segments are joined by an ether connecting linkage are known as Tergitol 15—S—X ™ and Triton CF ™ (Union Carbide, Danbury, Conn.). The general structural formula for these surfactants is as below:

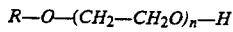

$$R-O-(CH_2-CH_2O)_n-H$$

wherein R is a $C_8$ to $C_{20}$ hydrocarbyl group and n is a number having a value from about 3 to 40 or more. Coatings made from compositions containing such a surfactant would be more hydrophilic than a coating made in its absence since the surfactant would remain in the coated film upon drying and not be removed except possibly by copious washing with water. Such surfactants would also be categorized as chemically stable, resisting all but the most severe acid, base or enzymatically catalyzed destructive processes. Loss of such surfactants in the waste streams from treatment baths constitutes a serious environmental problem, particularly when the hydrophobe is polyfluorinated.

Destructible nonionic surfactants are known. It is disclosed in U.S. Pat. No. 2,476,307 that a hydrolyzable silicon-containing compound of the formula:

$$C_{18}H_{37}Si[O(CH_2CH_2O)_4H]_3$$

is soluble in water to give a slightly cloudy solution useful for producing oil-in-water type emulsions that can render textile fiber water-repellent by a process in which the silicon ester hydrolyzes, splitting off the polyglycol radicals, and changing the residue into a polymer of an alkyl-siliconic acid. However, coating compositions containing solely such a silicon-containing compound would not produce an oil-repellent finish on a substrate.

U.S. Pat. No. 4,865,910 teaches the treatment of a glass fiber product with fluoroalkylsilanes of the formula:

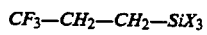

$$CF_3-CH_2-CH_2-SiX_3$$

wherein X represents a hydrolyzable group such as an alkoxy group, including 2-methoxyethoxy. Also taught is that fluoroalkylsilanes of the formulae:

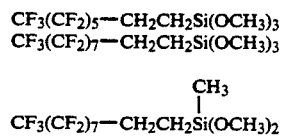

$$CF_3(CF_2)_5-CH_2CH_2Si(OCH_3)_3$$
$$CF_3(CF_2)_7-CH_2CH_2Si(OCH_3)_3$$

$$CF_3(CF_2)_7-CH_2CH_2\underset{\underset{CH_3}{|}}{Si}(OCH_3)_2$$

lack water solubility and that surface treatment with their methanolic solutions exhibits no effect.

U.S. Pat. Nos. 4,929,666 and 5,006,624 describe water-dispersible, crosslinkable polymeric surfactants having fluorocarbon and ionic moieties that can be cured into tough, solvent resistant, low critical surface tension coatings useful for protective finishes that adhere to most surfaces. Such polymeric surfactants require polyfunctional crosslinkers capable of reacting with the ionic moiety of the surfactant in order to cure.

Conventional methods for providing oil- and water-repellent coatings via aqueous delivery generally utilize a fluorochemical (resin or polymer) dispersed in water containing an external stable surfactant.

SUMMARY OF THE INVENTION

The background art does not describe a surfactant that would be useful for providing substrates with a coating by aqueous delivery wherein the coating does not exhibit decreased water or oil repellency due to residual surfactant present in the coating. The present invention teaches surfactants which chemically react with water, destroying their surfactancy and providing reaction products which become incorporated into the resulting coating and provide oil and water repellency.

Briefly, the present invention provides a destructible surfactant comprising a hydrophilic and a hydrophobic portion, the destructible surfactant comprising a fluorocarbylalkoxysilane comprising at least one polyfluorinated aliphatic or polyfluorinated ether group and at least one hydrophilic polyol, polyol ether, or polyoxyalkylene group which can be cleaved from the hydrophobe by hydrolysis. The liquid or low-melting solid, destructible nonionic surfactants are water soluble or dispersible, are useful as stabilizers for oil-in-water emulsions of fluorochemicals, and on curing alone or in conjunction with other fluorochemicals provide a layer on a substrate. The cured layer can provide the substrate with an oil- and water-repellent coating that is substantially free of surfactant.

The invention further provides an aqueous composition which upon hydrolysis and condensation provides a substrate with an oil- and water-repellent coating comprising:

1) a liquid, destructible nonionic surfactant comprising a fluorocarbylalkoxysilane comprising at least one polyfluorinated aliphatic group and at least one hydrolyzable hydrophilic polyoxyalkylene or polyol or polyol ether group;

2) optionally, one or more hydrocarbylalkoxysilanes or halocarbylalkoxysilanes comprising an alkyl or haloalkyl group comprising 1 to 24 carbon atoms and at least one $C_1$ to $C_4$ alkoxy group;

3) optionally a catalyst; and 4) water.

The invention also provides a process for providing a substrate with an oil- and water-repellent coating comprising the steps:

1) providing a substrate and an aqueous composition comprising a solution or dispersion of a fluorocarbylalkoxysilane destructible nonionic surfactant and optionally at least one additional silane and catalyst as described above;

2) coating the substrate with a layer of the composition of step 1 or immersing the substrate into the composition of step 1 for a time sufficient to form an adsorbed layer on the substrate;

3) drying the coating; and 4) curing the coating;

whereby the surface of the substrate is rendered oil- and water-repellent.

The destructible nonionic surfactants of the invention have a balance of properties between the oil- and water-repellent properties imparted by the polyfluorinated aliphatic groups and the water-associating hydrophilic properties imparted by the hydrophilic groups such that a one percent by weight mixture of the surfactant in water has a cloud point at a temperature from 0° to 100° C., preferably from 20° to 50° C. Surfactants with a cloud point below 0° C. and above 100° C. may have utility in some applications but they are generally less efficient. The hydrolysis reaction which is involved in the destruction of the nonionic surfactant and condensed layer formation can take place at room temperature but is accelerated at increased temperatures or in the presence of acid or base. The destruction mechanism involves catalyzed or uncatalyzed hydrolysis of the alkoxysilanes to provide silanols and alcohols. The silanols then undergo condensation to form crosslinked siloxane resins which can either phase separate as solid particles of various sizes depending on the conditions or adsorb as a layer on at least a portion of suitable substrates. Temperature, pH, substrate surface energy, surfactant concentration, and choice of catalyst, can be adjusted so as to control the rates of destruction and favor either particle or layer formation. The surfactants generally have maximum stability at a neutral pH.

In this application:

"surfactant" means a surface active compound capable of reducing interfacial tensions;

"water dispersible" includes those substances that in water will form a solution, a stable micellar or colloidal suspension, or a coarser suspension which is stable for a time suitable for its application;

"hydrocarbyl" means an organic group containing only carbon and hydrogen atoms;

"cloud point" means the temperature at which a 1 percent aqueous solution of a surfactant begins to phase separate, as indicated by developing cloudiness;

"polyfluorinated" means containing at least 30 weight percent fluorine atoms;

"fluorocarbyl" means a hydrocarbyl group that has been polyfluorinated; it can also contain ether oxygen;

"polyol or polyol ether group" means a radical derived from a polyol or polyol ether by removal of a hydroxyl hydrogen atom; and "group" means the stated radical or the radical substituted by any moiety that does not interfere with the intended function of the radical.

DESCRIPTION OF PREFERRED EMBODIMENTS

The destructible surfactants of the invention preferably have one of the general formulae:

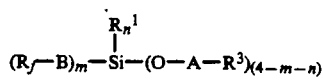

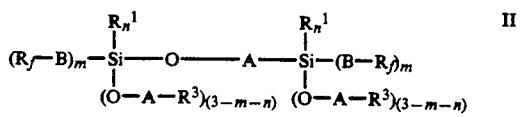

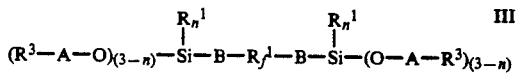

wherein:

each A is independently 1) a covalent bond, or 2) a divalent hydrophilic group (a) having the formula $(CHR^2-CH_2O)_q$ in which q is a number having a value of 1 to 40, preferably 2 to 10, $R^2$ is hydrogen or methyl, and that at least 70% of $R^2$ is hydrogen, or (b) derived from a polyol or its alkyl ether or polyether derivative by removal of one OH and one hydroxyl hydrogen, preferably derived from sorbitol or glycerol;

B is a divalent connecting group joining Si to $R_f$ or $R_f^1$, preferably comprising one or more of arylene (preferably phenylene), $-(CH_2)_s-$ and $-(CH_2)_s O-(CH_2)_s-$, but, in addition, comprising any divalent group that is substantially stable against hydrolysis such as the divalent amide groups

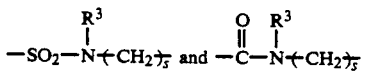

in which s and s' are independently integers of 1 to 12 and $R^3$ is defined below;

$R_f$ is a (1) monovalent polyfluoroaliphatic group having 2 to 24, preferably 4 to 12, more preferably 6 to 10, carbon atoms, the terminal carbon of which group preferably having three fluorine atoms, and at least 30 weight percent fluorine; it is, preferably, a straight chain or branched polyfluoroaliphatic group having 2 to 24 carbon atoms, preferably 4 to 12 carbon atoms, or cyclic polyfluoroaliphatic group having 4 to 24 carbon atoms, any of the aliphatic groups optionally containing oxygen bonded only to carbon atoms, optionally comprising chlorine atoms, provided that not more than one atom of either of hydrogen or chlorine is present for every two carbon atoms, and preferably provided that hydrogen is not at the distant chain terminus; or (2) a monovalent polyfluoroalkoxy poly(fluorooxyalkylene) group having a number average molecular weight of 250 to 2,000; it is, more preferably, a straight chain, branched, or cyclic perfluoroaliphatic group having 4 to 12 carbon atoms;

$R_f^1$ is a divalent polyfluoroaliphatic group having at least 6 carbon atoms and at least 30 weight percent of fluorine atoms; it is, preferably (1) a divalent straight chain, branched chain, or cyclic polyfluoroaliphatic group having 6 to 24 carbon atoms, optionally containing chlorine atoms, or oxygen bonded only to carbon atoms, provided that no more than one atom of either hydrogen or chlorine is present for every two carbon atoms, or (2) a divalent poly(fluorooxyalkylene) group having a number average molecular weight of 300 to 2,000;

$R^1$ is an alkyl group having 1 to 18 carbon atoms or phenyl;

$R^2$ is hydrogen, or methyl, no more than 30% of $R^2$ being methyl;

$R^3$ independently is hydrogen or lower alkyl group having 1 to 4 carbon atoms;

m independently is an integer having a value of 1, 2, or 3;

n independently is zero or an integer having a value of 1 or 2;

m+n has a sum total value of 1, 2, or 3;

with the provisos that at least one of A is a divalent hydrophilic group, preferably $-(CHR^2-CH_2O)_{\overline{q}}$, and that the ratio of $R_f$ or $R_f^1$ groups to hydrophilic groups is such that a one percent mixture by weight of the surfactant in water has a cloud point in the range of 0° C to 100° C, preferably 20° C. to 50° C.

The destructible surfactants of the invention are prepared by processes well known in the art. Generally, the surfactants of Formula I are prepared by heating one or up to 4-m-n or more equivalent weights of polyoxyalkylene alcohol, which are commercially available or can be prepared by methods known in the art, having the formula $$HO-A-A^3 \quad \text{IV}$$

in which A and $R^3$ are defined above, with one equivalent weight of polyfluoroaliphatic alkoxysilane, which are commercially available or can be prepared by methods known in the art, having the formula

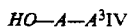

V in which $R_fB$, $R^1$, m, and n are defined above and $R^5$ is a lower alkyl group of 1 to 4 carbon atoms, optionally in the presence of a catalyst such as toluenesulfonic acid. It is to be appreciated that the alcohol exchange reaction may be incomplete and any sample may comprise different mixtures of "A" groups.

Alternatively, the surfactants of Formula I are prepared by reaction of 4-m-n or more equivalent weights of the polyoxyalkylene alcohol of Formula IV with one equivalent weight of a polyfluoroaliphatic halosilane, which is commercially available or can be prepared by methods known in the art, having the formula:

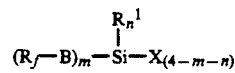

VI in which X is a halogen, preferably chlorine, and $R_f$, $R^1$, B, m, and n are defined above, in the presence of an acid acceptor such as triethylamine or sodium methoxide.

The surfactants of Formula II will occur to some extent in the reaction product form the preparation of the surfactants of Formula I when $R^3$ is hydrogen. With use of decreasing mole ratios of polyoxyalkylene alcohol, HO-A-$R^3$ wherein $R^3$ is hydrogen, to polyfluoroaliphatic alkoxysilane,

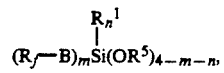

or polyfluoroaliphatic halosilane,

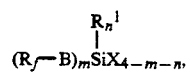

an increasing amount of surfactant of Formula II will be obtained.

Destructible surfactants of Formula III are prepared by reacting 2(3-n) equivalent weights of polyoxyalkylene alcohol of Formula IV with one equivalent weight of the polyfluoroaliphatic halosilane of the formula:

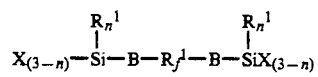

VII

Alternatively, they are prepared by the reaction of one or up to 2(3-n) or more equivalent weights of the polyoxyalkylene alcohol of Formula IV with one equivalent weight of the polyfunctional polyfluoroaliphatic bisalkoxysilane having the formula,

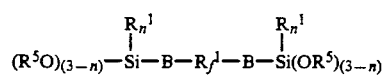

VIII wherein $R^5$, $R_f^1$, B, $R^1$, and n are as defined above. Compounds of formulae VII and VIII are disclosed, for example, in U.S. Pat. No. 3,810,874.

These preparations and water reactivity of these materials can be summarized in "Chemical Reactions" below, wherein $R^1$, $R^3$, A, B, Rf, $R_f^1$, m, and n are as previously defined:

Chemical Reactions hydrophilic polyol, polyol ether, or polyoxyalkylenealcohol
+
polyfluoroaliphatic halo- or alkoxysilane

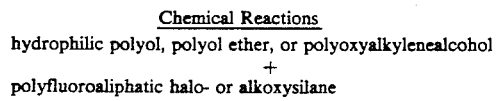

any of destructible surfactants I, II, and III

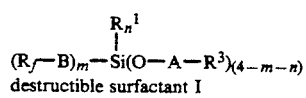
destructible surfactant I

-continued
Chemical Reactions

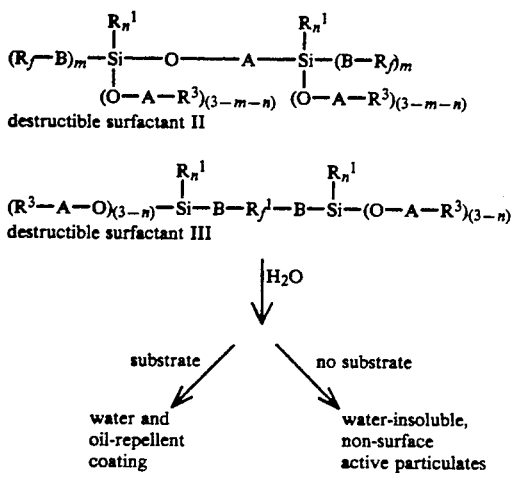
destructible surfactant II $(R^3-A-O)_{(3-n)}-\overset{R_n^1}{\underset{|}{Si}}-B-R_f^1-B-\overset{R_n^1}{\underset{|}{Si}}-(O-A-R^3)_{(3-n)}$
destructible surfactant III

↓ H₂O substrate / \ no substrate water and oil-repellent coating / water-insoluble, non-surface active particulates Polyoxyalkylene alcohols of Formula IV suitable for use in the preparation of the surfactants of the invention have a molecular weight up to about 1500. Many are commercially available and are sold under the trademark "Carbowax" and "Cellosolve" (available from Aldrich Chemical Co., Milwaukee, Wis.). Preferred polyoxyalkylene alcohols include di- to heptaethyleneglycols and their monomethyl and monoethyl ethers.

Examples of preferred polyfluoroaliphaticsilanes of Formulae V, VI, VII, and VIII suitable for use in the preparation of the surfactants include $C_5F_{11}CH_2OCH_2CH_2CH_2Si(OCH_2CH_3)_3$
$C_7F_{15}CH_2OCH_2CH_2CH_2Si(OCH_2CH_3)_3$
$C_7F_{15}CH_2OCH_2CH_2CH_2SiCl_3$
$C_8F_{17}CH_2CH_2OCH_2CH_2CH_2SiCl_3$
$C_{18}F_{37}CH_2OCH_2CH_2CH_2SiCl_3$ $\underset{\underset{CF_2Cl}{|}}{CF_3CFCF_2CF_2SO_2NCH_2CH_2CH_2SiCl_3}\ \ \underset{CH_3}{|}$ $\underset{\underset{CH_2CH_3}{|}}{C_8F_{17}SO_2NCH_2CH_2CH_2Si(OCH_3)_3}$ $\underset{\underset{CH_3}{|}}{C_8F_{17}SO_2NCH_2CH_2CH_2Si(OCH_3)_3}$ $\underset{\underset{C_7F_{15}CH_2CH_2SiCl_2}{}}{\overset{CH_3}{|}}$ $C_8F_{17}CH_2CH_2SiCl_3$
$Cl_3SiCH_2CH_2CH_2OCH_2(OCF_2CF_2)_8CH_2OCH_2CH_2CH_2SiCl_3$ $\underset{\underset{CF_3}{|}}{CF_3(CF_2CF)_4CF_2\overset{O}{\overset{||}{C}}NHCH_2CH_2CH_2Si(OC_2H_5)_3}$ $CF_3O(C_3F_6O)_4(CF_2O)_3CF_2CH_2O\overset{O}{\overset{||}{C}}NHCH_2CH_2CH_2Si(OCH_3)_3$ $Cl_3SiCH_2CH_2CH_2OCH_2(CF_2CF_2O)_8(CF_2O)_4CF_2CH_2CH_2CH_2SiCl_3$ The polyfluoroaliphatic silanes of Formulas V and VI may be prepared by the hydrosilation of a vinylic compound such as $R_fCH_2OCH_2CH=CH_2$, $\underset{\underset{}{}}{R_fSO_2\overset{R^3}{\underset{|}{N}}CH_2CH=CH_2}$, or $R_fCH=CH_2$, wherein $R_f$ is as defined above, with a silane of the formula $H_m\overset{R_n^1}{\underset{|}{Si}}(OR^5)_{4-m-n}$ or $H_m\overset{R_n^1}{\underset{|}{Si}}X_{4-m-n}$ wherein $R_1$, $R^5$, X, m and n are as defined above. These silanes are available from H s America, Inc., Piscataway, N.J. Examples of this chemistry are given in Steward and Pierce, J. Org. Chem. 1961, 26, 2643. The allyl ethers or N-allylsulfonamides can be prepared by alkylation of the corresponding alcohol $R_fCH_2OH$ or sulfonamide $R_fSO_2NMR^3$ with, e.g., allyl bromide, in accordance with methods well known in the art. The polyfluoroaliphatic bis(silanes) of Formulae VII and VIII where B is —$CH_2OCH_2CH_2CH_2$— are prepared similarly by hydrosilation of the bisallyl ether $H_2C=CHCH_2OCH_2R_f^1CH_2OCH_2CH=CH_2$ with $H\overset{R_n^1}{\underset{|}{Si}}(OR^5)_{3-n}$ or $H\overset{R_n^1}{\underset{|}{Si}}X_{3-n}$.

Compounds having the formula $R_fCONH(CH_2)_3\overset{R_n^1}{\underset{|}{Si}}(OR^5)_{3-n}$ can be prepared by treatment of esters of $R_fCO_2H$ with an aminosilane, e.g., $NH_2(CH_2)_3Si(OCH_3)_3$. These aminosilane compounds are available from Hüls or Aldrich, and many of the carboxylic acids are available from PCR, Gainesville, Fla.

Nonsurfactant hydrocarbylalkoxysilanes and fluorocarbylalkoxysilanes can be used in the aqueous composition of the invention. Their use is optional and they can be included as crosslinkers, extenders, or chain terminators in the composition depending on whether t is formula IX or 0 or 1, 2, or 3, respectively. These compounds are dispersible in the presence of the destructible surfactants. Included among suitable compounds are those having the formula $R^6_tSi(OR^5)_{4-t}$  IX many of which are commercially available, in which $R^5$ is a lower alkyl group of $C_1$ to $C_4$, t is an integer having a value of 0, 1, 2, or 3, and $R^6$ is $R_f$—B as defined above or a monovalent group selected independently from alkyl groups having 1 to 24 carbon atoms, and aryl, alkaryl, or aralkyl groups having 6 to 12 carbon atoms.

Examples of suitable hydrocarbylalkoxysilanes (many of which are available from Union Carbide, Dow Corning, Aldrich, or Hüls) include: methyltriethoxysilane, dimethyldiethoxysilane, butyltriethoxysilane, octyltrimethoxysilane, dodecyltriethoxysilane, octadecyltriethoxysilane, phenyltriethoxysilane, the corresponding chlorosubstituted alkylalkoxysilanes such as chloromethyltriethoxysilane, chlorobutyltriethoxysilane, 3-(2,2,2-trifluoroethoxy)propyltriethoxysilane, 3-(N-alkyl-perfluorooctylsulfonamido)propyltrimethoxysilane, 3-(perfluoroheptylmethoxy)propyltrimethoxysilane, and tetraethoxysilane.

Useful substrates for the surfactants of the invention include textiles such as cotton, polyester, acrylic, nylon, polyolefins such as polypropylene, wool, or combinations of the foregoing, and glass, ceramics, metals, concrete and masonry.

The surfactants of the invention are useful in preparing oil- and water-repellent coatings on these substrates via aqueous delivery, preparation of hydrophobic filler particles, transient stabilization of oil/water emulsions or dispersions, and generation of low surface tensions in coating media where transient low tension is desired due to environmental or waste disposal considerations, or where residual surfactant in the resultant coating is undesirable. The coatings generally are less than 5 micrometers thick, preferably less than 2 micrometers thick.

Fabrics treated with the destructible surfactants of the invention were tested for repellency by the following methods:

A. Water Repellency Test (WR)

The aqueous stain or water repellency of treated samples is measured using a water/isopropyl alcohol test, and the result is expressed in terms of a water repellency rating of the treated fabric. Treated fabrics which are penetrated by or resistant only to a 100 percent water/zero percent isopropyl alcohol mixture (the least penetrating of the test mixtures) are given a rating of 0, whereas treated fabrics resistant to zero percent water/100 percent isopropyl alcohol mixture (the most penetrating of the test mixtures) are given a rating of 10. Other intermediate values are determined by use of other water/isopropyl alcohol mixtures, in which the percentage amounts of water and isopropyl alcohol are each multiples of 10. Results are reported as an average of replicate testing. The first water repellency rating (not in parentheses) corresponds to the most penetrating mixture which does not penetrate or wet the fabric after 10 seconds contact as measured by retention of air on the fabric surface under the droplet. The second water repellency rating (in parentheses) corresponds to the most penetrating mixture which is not completely wicked into the fabric in 10 seconds. Higher number ratings indicate better static water repellency.

B. Oil Repellency Test (OR)

The oil repellency of treated carpet and textile samples is measured by the American Association of Textile Chemists and Colorists (AATCC) Standard Test Method No. 118-1983, which test is based on the resistance of treated fabric to penetration by oils of varying surface tensions. Treated fabrics resistant only to Nujol ™ (Plough, Inc.), a brand of mineral oil and the least penetrating of the test oils, are given a rating of 1, whereas treated fabrics resistant to heptane (the most penetrating of the test oils) are given a value of 8. Other intermediate values are determined by use of other pure oils or mixtures of oils, as shown in the following table:

| Standard Test Liquids (as described in AATCC Test Method 118-1983) | |
|---|---|
| AATCC Oil Repellency Rating Number | Composition |
| 1 | mineral oil |
| 2 | 65:35 mineral oil:hexadecane by volume |
| 3 | n-hexadecane |
| 4 | n-tetradecane |
| 5 | n-dodecane |
| 6 | n-decane |
| 7 | n-octane |
| 8 | n-heptane |

The first oil repellency rating corresponds to the most penetrating oil (or mixture of oils) which does not penetrate or wet the fabric after 30 seconds contact as measured by retention of air on the fabric surface under the droplets. The second rating in parentheses corresponds to the most penetrating oil which is not completely wicked into the fabric in 30 seconds. Higher numbers indicate better oil repellency.

C. Dynamic Water Repellency (Wa and WT)

To evaluate the dynamic wettability of fabrics treated with the silanes of this invention we chose to report the weight percent moisture absorption (Wa) and wet through volume (WT) using the standard Bundesman apparatus (DIN 53 888, German Standards DK 677.064:620 193.2 August 1965). Circular samples of 140 mm diameter silane treated fabrics equilibrated with ambient atmospheric moisture for 24 hours after a 150° C., 5-minute cure step, mounted on cups such that the exposed area is 80 cm$^2$ and tilted away from horizontal by 15°, are showered with rain drops of approximately 0.07 ml each from a distance of 150 cm at 65° F. using typical municipal water for a period of 5 minutes at 100 ml/min over an area of 100 cm$^2$; the samples were then centrifuged on a horizontal disc at 700 rpm for one minute. The moisture retention in the fabric (Wa), measured as the percent increase in weight of the thus treated fabric, and the volume of collected water in the cup passed by the fabric (WT), are reported. Such measures differentiated the treatments of fabrics at the 0.5 wt. % solids on fabric level by destructible and stable surfactant delivered emulsions where the standard spray rating test (SR, AATCC Test Method 22-1971) did not.

Objects and advantages of this invention are further illustrated by the following examples, but the particular materials and amounts thereof recited in these examples, as well as other conditions and details, should not be construed to unduly limit this invention. In the examples all parts and percentages are by weight and temperatures are in degrees centigrade unless otherwise noted. Unless otherwise indicated, all parts are by weight, and Me=methyl, and Et=ethyl.

EXAMPLES

Preparation of fluorocarbylalkoxysilane surfactants of structural formula I

EXAMPLE 1

A 250 ml 3-necked round bottom flask was equipped with magnetic stirrer, thermometer, addition funnel and ice bath. A stream of dry nitrogen was introduced and the flask charged with a solution of 10 g (17.4 mmol) of $C_7F_{15}CH_2O(CH_2)_3SiCl_3(1)$ in 75 ml Of diethylether. (The silane was prepared from $C_7F_{15}CH_2OCH_2CH=CH_2$ and trichlorosilane as described in U.S. Pat. No. 3,012,006 Ex. 1. The allyl compound was prepared by reaction of allyl bromide with $C_7F_{15}CH_2OH$ in the presence of KOH, using dimethylsulfoxide (DMSO) as solvent.) Stirring was initiated and a solution of 6.88 g (57.3 mmol) diethylene glycol monomethyl ether (Aldrich, distilled from sodium) and 5.8 g (57.4 mmol) triethylamine in 50 ml of diethyl ether was introduced dropwise through the addition funnel. An exotherm to 25° C. occurred. The ice bath was removed and the solution was allowed to stir overnight. The reacted mixture was filtered to remove amine salt and the filtrate was distilled to remove ether leaving 14.7 g clear virtually colorless liquid. A 2.0 g portion of this liquid was distilled in a Kugelrohr apparatus yielding 1.68 g of product fraction having a boiling point of 165°-175° C./0.04 torr. The $^1H$ NMR spectrum of this fraction was consistent with the above-stated product. It was designated surfactant-1.

EXAMPLE 2

$C_7F_{15}CH_2O(CH_2)_3Si[O(CH_2CH_2O)_3CH_3]_3$

The procedure of Example 1 was repeated using an equivalent amount of triethylene glycol monomethyl ether (Aldrich, distilled from calcium hydride) in place of the diethylene glycol monomethyl ether. Vacuum stripping of the reaction mixture to 120° C./0.1 torr gave an 89% yield of clear, slightly straw-colored liquid residue. The $^1H$ NMR spectrum of this product was consistent with the above-stated product. The product was designated surfactant-2.

EXAMPLE 3

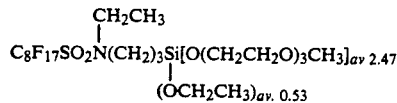

A 15 ml round bottom flask equipped with oil bath heating, magnetic stirrer, Microware ™ short-path distilling head, and nitrogen blanket was charged with 5 g (6.8 mmol) $C_8F_{17}SO_2N(Et)(CH_2)_3Si(OPEt)_3(2)$ (prepared by reaction of $C_8F_{17}SO_2N(Et)CH_2CH=CH_2$, which can be obtained as described in U.S. Pat. No. 3,442,664 (Ex. 1), with $HSi(OEt)_3$ and Pt/divinyltetramethyldisiloxane as hydrosilation catalyst) and 3.45 g (21 mmol) triethylene glycol monomethyl ether (Cellosolve ™, Union Carbide, available from Aldrich). The resulting two-phase mixture was stirred and heated in an oil bath at 150° C. After several minutes the mixture had become homogeneous and distillate began to collect. When volatiles evolution had slowed, another 1.53 g triethylene glycol monomethyl ether was added and the bath temperature was increased to 200° C. After another 15 minutes the flask was removed from the bath and allowed to cool. The product was vacuum stripped by heating in a Kugelrohr ™ apparatus from room temperature up to 150° C./0.03 torr, yielding 2.24 g distillate (discarded) and 6.29 g (85% yield) clear, slightly yellow liquid. NMR data on this material showed that complete replacement of ethoxy groups had not been achieved, and the average composition was 0.53 ethoxy and 2.47 glycol alkoxy groups per silicon. The product was designated surfactant-3.

EXAMPLE 4

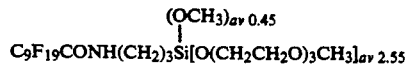

Using an apparatus analogous to that in Example 3, a mixture of 20.0 g (29.6 mmol) molten $C_9F_{19}CONH(CH_2)_3Si(OMe)_3(3)$ (prepared by reaction of $C_9F_{19}CO_2CH_3$ with 3-aminopropyltrimethoxysilane) and 18.95 g (115.6 mmol) triethylene glycol monomethyl ether was heated and stirred in an oil bath at 200° C. Collection of distillate began after a few minutes and proceeded until 2.75 g had accumulated (theoretical yield of methanol, 2.84 g). The flask was removed from the bath and allowed to cool. The dark brown liquid residue was vacuum stripped in a Kugelrohr apparatus up to 180° C./0.03 torr, giving 5.54 g distillate (discarded) and 30.21 g (95% yield) dark residue. NMR analysis of this residue showed approximately 0.45 methoxy and 2.55 glycol alkoxy groups per silicon. It was designated surfactant-4.

EXAMPLE 5

$C_{17}F_{15}CH_2O(CH_2)_3Si(OCH_2CH_2OCH_2CH_2OH)_3$
(average composition)

A mixture of 5 g (8.3 mmol) $C_7F_{15}CH_2O(CH_2)_3Si(OEt)_3(4)$ prepared using the procedure of Example 1 (except for replacing the $HSiCl_3$ with $HSi(OEt)_3$), and 2.64 g (24.9 mmol) diethylene glycol (Aldrich Chemical Co.) was heated in a 25 ml round bottom flask equipped with oil bath, magnetic stirrer, Microware short path distilling head, and nitrogen blanket, up to a bath temperature of 215° C. Distillate collection began when the bath reached 180° C. A total of 1.1 g volatiles was collected. It was necessary to heat the distilling head with a heat gun to maintain flow during the latter stages of the distillation. The flask was removed from the bath and allowed to cool, and the crude product was vacuum stripped at 100° C/2 torr to remove the last traces of ethanol. This left 6.47 g (quantitative yield) clear, nearly colorless liquid product. While the $^1H$ NMR spectrum of this product was fairly consistent with the desired structure, $^{29}Si$ NMR data revealed the presence of more than one component, suggesting that cyclic and oligomerized materials may also have formed. This product was designated surfactant-5.

EXAMPLE 6

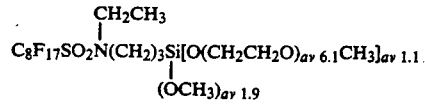

The general procedure of Example 3 was repeated using $C_8F_{17}SO_2N(Et)(CH_2)_3Si(OMe)_3(5)$ (prepared by treatment of $C_8F_{17}SO_2N(Et)CH_2CH=CH_2$ with $HSiCl_3$ in the presence of Pt/divinyltetramethyldisiloxane as catalyst, followed by treatment of the product with methanol and triethylamine in $CF_2ClCFCl_2$ as solvent) and only 1.1 equivalents of poly(ethylene glycol) monomethyl ether that had a hydroxyl equivalent weight of 300. The product obtained was designated surfactant-6.

EXAMPLE 7—Preparation of Difunctional bis(trialkoxysilane) surfactant (surfactant-7) of structural Formula III Fifty grams perfluoropolyether ester $X$—$CF_2O(C_2F_4O)_nCF_2$—$X$ (A) in which $X=$—$COOCH_3$ and —$OCF_3$ (85% carboxyfunctionalized) and $n_{av}$ is approximately 8.6 (ester equivalent weight approximately 600), prepared using methods described in U.S. Pat. No. 5,093,432, Example 9, and WO 92/12199, p. 15, was stirred overnight at room temperature with 11.7 g 3-aminopropyltrimethoxysilane. Upon return, IR analysis showed significant ester remaining, so more amine was added in portions until the ester carbonyl band had vanished. The total amount of amine added was 15.02 g. The product was vacuum stripped to remove the methanol byproduct and any remaining unreacted aminosilane. Twenty grams of the above product was mixed with 14.57 g triethylene glycol monomethyl ether (Aldrich) and heated by oil bath in a 100 ml roundbottom flask equipped with magnetic stirring, short-path distilling head, receiver, and nitrogen blanket. Distillation of volatiles began when the oil bath reached 150° C. Heating was continued up to 210° C. whereupon evolution of volatiles ceased. This gave 2.87 g distillate (discarded). The residue, a clear brown liquid, was vacuum stripped at 150° C./0.07 torr to remove excess alcohol, leaving 26.8 g product which exhibited NMR spectra consistent with the structure A in which $X=$—$OCF_3$ and —$CONH(C_3H_6)Si(OMe)_x(0(C_2H_4O)_3CH_3)Y$ in 15:85 molar ratio where x and y were, on average, 0.09 and 2.91 respectively. The $^{29}Si$ NMR spectrum also showed evidence of condensation products at low levels. The above silane product, designated surfactant-7, was found to be soluble in water at least up to 2 wt. % giving clear solutions showing good foaming on shaking. The solutions remained clear for about minutes before precipitation of solid was noted. This product was found to have greater stability to precipitation when dissolved in a pH 7 buffer solution instead of water. (The buffer was prepared by diluting one part (by volume) pH 7 phosphate buffer (EM Science) in four parts (by volume) Mohm water obtained from a Millipore filtration system to reduce the effect of phosphate ion on silane hydrolysis and condensation. Its surface tension was found to be 74 dynes/cm at room temperature when measured by the Wilhelmy method with a 2 mm quartz rod probe.) A fresh 0.1 wt. % solution of silane surfactant-7 in this buffer exhibited a surface tension of 19 dyn/cm before and after filtration through a syringe filter. After aging six days at room temperature, the solution had developed a small amount of solid precipitate; this was removed by syringe filtration. The surface tension was then remeasured and found to be dyn/cm.

EXAMPLE 8 —Preparation of Higher-MW Bis(Trialkoxysilane) Surfactant (Surfactant-S) of Structural Formula III Perfluoropolyether bis(triethoxysilane) $X$—$CF_2O(CF_2)_a(C_2F_4O)_bCF_2$—$X$ where $a_{av}\approx 12$, $b_{av}\approx 10$, and $X=$—$CONHC_3H_6Si(OEt)_3(6)$ was prepared according to U.S. Pat. No. 3,810,874, Table 1, line 6. This product (15.00 g) was mixed with 8.14 g poly(ethylene glycol) monomethyl ether, 0H equivalent weight 300 (MPEG 350, Aldrich) in a 100 ml roundbottom flask equipped with oil bath heating, magnetic stirring, short-path distilling head and nitrogen blanketing attachments. The alcohol charged was sufficient to replace approximately four, on average, of the six ethoxy groups. Heating and stirring were begun, with the mixture showing two liquid phases until the bath temperature reached about 185° C. at which point the reaction mixture became homogeneous and evolution of volatiles began. Heating was continued to a bath temperature of 220° C. at which point evolution of the volatiles ceased. This gave 1.23 g distillate, boiling range 75°-85° C., which was discarded (theoretical yield of ethanol, 1.25 g). An attempt to vacuum strip the product at pressures below 1 torr was unsuccessful because of severe foaming. Yield of product, designated surfactant-8, was 21.2 g. A 1 wt. % mixture of this product in water gave a clear solution which foamed on shaking, and gradually developed precipitate (while foaming diminished) over a period of about 30 min as the silane hydrolyzed and condensed. A fresh 1 wt. % solution of surfactant-8 in water was diluted immediately to 0.1 wt. % in the pH 7 buffer described in the previous example. The surface tension of this solution was found to be 26 dyn/cm when fresh, and 53 dyn/cm after 48 hours at room temperature.

EXAMPLE 9 —Preparation of Surfactant-9 with Structural Formula II

A 100-ml roundbottom flask equipped with oil bath heating, magnetic stirring, short-path distilling head and nitrogen blanketing attachments was charged with 11.5 g (0.02 mole) $C_7F_{15}CONHCH_2CH_2CH_2Si(OCH_3)_3(7)$ (prepared by treating $C_7F_{15}CO_2CH_3$ (can be obtained from PCR, Gainesville, Fla.) With an equimolar amount of 3-aminopropyltrimethoxysilane (Hüls) and vacuum distilling the product at 130°-140° C./0.09 torr) and 2.5 g polyethylene glycol (PEG-1000 TM (OH titrimetric equivalent weight 552, 0.0045 mole OH), Aldrich, dried before use by azeotropic distillation of water with excess cyclohexane). The two-phase mixture was heated and stirred, gradually raising the oil bath temperature to 210° C. and maintaining this temperature for 30 minutes. Methanol was removed by application of aspirator vacuum via the short path head distilling attachments; then the residue was allowed to cool. Vacuum stripping using a Kugelrohr device at 160° C./0.02 torr to remove excess silane gave 9.09 g distillate (discarded) and 4.68 g clear, brown liquid, designated surfactant-9. Analysis of this product by proton and silicon NMR spectroscopy gave spectra consistent with the following structure as the major component:

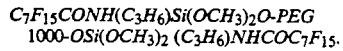
$C_7F_{15}CONH(C_3H_6)Si(OCH_3)_2O$-PEG
1000-$OSi(OCH_3)_2(C_3H_6)NHCOC_7F_{15}$.

Magnetically stirring a mixture of 0.25 g above product, surfactant-9, and 24.75 g distilled water in a vial for about 2 hours at about 23° C. gave a slightly colored, virtually clear solution showing extensive foaming when shaken. Heating with a heat gun while hand-shaking a mixture of 0.1 g surfactant and 19.9 g water in a vial gave a cloudy dispersion which clarified on cooling to room temperature together with an extremely viscous and stable foam phase. The surface tension of the 1 wt. % aqueous solution prepared by magnetic stirring was 28 dyn/cm after 5 hours at room temperature, and 53 dyn/cm after 124 hours at room temperature.

EXAMPLE 10—Illustrating the Destruction of Fluorocarbylalkoxysilane Surfactants Surface tension of aqueous solutions of fluorocarbylalkoxysilanes designated surfactant-1 to surfactant-5 at various concentrations, as shown in TABLE I, below, was measured by the Wilhelmy plate method.

Solutions containing various concentrations of the products described in the above examples were prepared in 18 Mohm Millipore-grade filtered deionized water. Surface tensions of these solutions at room temperature (20°-23° C.) were measured by dynamic contact angle analysis (Cahn DCA-322 TM) with a plasma-cleaned 2-mm diameter quartz rod probe at 90 micrometers/sec, after aging the solutions for the indicated times. The unbuffered pH of each solution was 6-7, as measured by EM-Reagents ColorpHast TM 4.0-7.0 indicator strips. Results from these static surface tension measurements, along with those for pure water, appear in TABLE I. All concentrations were by weight.

TABLE I

| Fluorocarbyl-alkoxysilane | Conc. ppm | Solution dye | Surface tension (dyn/cm) |
|---|---|---|---|
| surfactant 1 | 47 | 15 min | 20.7 |
|  | 100 | 120 min | 19.4 |
| surfactant 2 | 25 | 45 min | 25.7 |
|  | 25 | 4 days | 71.7 |
|  | 100 | 75 min | 21.9 |
|  | 100 | 4 days | 40.8 |
|  | 320 | 45 min | 22.7 |
|  | 320 | 2 days | 18.4 |
|  | 320 | 7 days | 21.6 |
|  | 320 | 14 days | 73.5 |
| surfactant 3 | 50 | 90 min | 21.4 |
| surfactant 4 | 186 | 30 min | 22.7 |
|  | 186 | 1 day | 69.1 |
| surfactant 5 | 206 | 15 min | 24.5 |
| water (comparative) | — | — | 72.5 |

The data of TABLE I shows that at an unbuffered neutral pH in water fluorocarbylalkoxysiloxane surfactant-2 at 25 ppm had completely decomposed in 4 days. At 320 ppm surfactant-2 solution had not completely decomposed in 7 days but had in 14 days (i.e., when the surface tension of the solution essentially equaled that of water the surfactant had decomposed totally). After complete decomposition of the surfactant the pH of these solutions was unchanged.

EXAMPLE 11 —Illustrating the Treatment of Cotton to Render it Water and Oil Repellent Into a 250 ml screw-top jar were placed 58 g distilled water, 0.03 g destructible fluorocarbylalkoxysilane surfactant-6, 2.91 g cotton fabric and 0.3 g of a 1.0 wt. % solution of sulfuric acid in water. The jar was capped and agitated at 25° C. for 3.5 hours. The fabric was removed and heated at 150° C. for 5 minutes. The recovered treatment solution showed no foaming upon shaking, implying that silane surfactant-6 had destructed. The treated fabric gave oil repellency (OR) 4(6) and water repellency (WR) 2(6) whereas the untreated fabric gave OR 0(0), WR 0(0), as determined by the oil and water repellency tests.

EXAMPLE 12 - Illustrating the Effect of Thermal Curing Conditions on the Repellency of Surfactant-3-Treated Wool Into a 500 ml screw-top jar were placed 280 g distilled water and 0.08 g destructible fluorocarbylalkoxysilane surfactant-3 and the mixture was shaken until the silane had dissolved. 4.2 g of 1% aqueous sulfuric acid and 14.00 g wool test fabric swatches were added. In a similar fashion another 500 ml jar was charged with 256 g distilled water, 0.07 g destructible fluorinated surfactant-3, 1.28 g 1% aqueous sulfuric acid, and 12.85 g wool/PE (polyester) blend test fabric swatches. The jars were shaken on a mechanical agitator overnight at 25° C. The swatches were then removed from the jars, blotted on paper towels to remove excess water and oven-cured under various conditions as shown in TABLE II. The samples were then tested for static oil and water repellencies using the methods previously described (see Tests A and B, above), with the results shown in TABLE II along with data for untreated fabrics.

TABLE II

| Fabric treated with Surfactant-3 | Post Treatment Cure Conditions | Oil Repellancy Treated | Oil Repellancy Untreated | Water Repellency Treated | Water Repellency Untreated |
|---|---|---|---|---|---|
| wool | RT**/7 days | 6(6) | 0(0) | 3(8) | 1(1) |
| wool | 125° C./5 min | 6(8) |  | 3(6) |  |
| wool | 150° C./5 min | 6(8) | 0(0) | 4(7) | 1(1) |
| wool | 175° C./5 min | 6(7) |  | 4(7) |  |
| wool/PE | RT/10 days | 1(1) | 0(0) | 2(3) | 1(2) |
|  | 125° C./5 min | 5(6) |  | 4(8) |  |
|  | 150° C./5 min | 4(6) | 0(0) | 4(8) |  |
|  | 175° C./5 min | 5(6) |  | 5(8) | 0(1) |

**RT = room temperature (20-23° C.)

The data in TABLE II show that both wool and wool/PE fabric were rendered oil- and water-repellent by treatment with an acidified aqueous solution of surfactant-3 and post curing at 125° to 175° C. for 5 minutes and that wool fabric was even made oil and water repellent when allowed to stand at room temperature for 7 days. Untreated wool and wool/PE fabrics were not oil or water repellent.

EXAMPLE 13 —Illustrating the Exhaustion of Fluorochemical Silane/Hydrocarbon Silane Mixtures and Hydrocarbon Silanes Alone on Wool Silanes $RSi(OC_2H_4OC_2H_4OC_2H_4OCH_3)_3$ ($R = C_{12}H_{25}$, $C_{18}H_{37}$), referred to below as $C_{12}$ and $C_{18}$ silanes, were prepared according to procedures described in U.S. Pat. No. 2,476,307, Example 1 by heating $RSi(OEt)_3$ (Hüls) with an excess of triethylene glycol monomethyl ether (Aldrich), distilling out the ethanol by-product, and removing excess glycol ether by vacuum stripping. Methyltrimethoxysilane (Aldrich) (MTMS) and tetraethylorthosilicate (Aldrich) (TEOS) were used without further purification. A 500 ml wide-mouth jar was charged with a mixture of 0.039 g of a fluorochemical silane analogous to surfactant-3, except prepared from the trimethoxysilane (surfactant-3A), and 0.039 g of the above-mentioned $C_{18}$ silane. Water (300 g) was added, the mixture was stirred to dissolve the silanes, then 4.7 g 1 wt. % aqueous sulfuric acid catalyst solution was added followed by 15.62 g 100% wool test fabric swatches. Analogous samples were prepared, using approximately 15 g wool and 30 wt. %

(based on fabric) 1 wt. % catalyst solution in each, with a 1:1 surfactant-3A:$C_{12}$ silane mixture, 1:1 surfactant-3A:TEOS mixture, $C_{18}$ silane alone, $C_{12}$ silane alone, and methyltrimethoxysilane alone, all at 0.5 wt. % solids based on fabric. The jars were capped and placed on a shaker at room temperature for 18 hours. The fabric swatches were removed, blotted on paper towels, then placed in an oven at 150° C. for 5 minutes. Evaluations of static oil and water repellencies (see Test A and B above) gave the results shown in TABLE III below.

TABLE III

| Silane(s) | OR | WR |
|---|---|---|
| 1:1 surfactant-3A:$C_{18}$ | 6(7) | 7(8) |
| 1:1 surfactant-3A:$C_{12}$ | 5(6) | 5(7) |
| 1:1 surfactant-3A:TEOS | 6(6) | 4(6) |
| $C_{18}$ (comparative) | 0(0) | 2(2) |
| $C_{12}$ (comparative) | 0(0) | 2(2) |
| MTMS (comparative) | 0(0) | 1(2) |

These results show that the prior art $C_{18}$ and $C_{12}$ hydrocarbon silanes exhibit very poor repellencies when applied alone to the wool fabric, but can be used in combination with the fluorochemical silane in accordance with the invention. Surprisingly, even the water repellencies of the $C_{12}$ and $C_{18}$ silanes used alone were poorer than those of the fluorinated silanes of this invention. Methyltrimethoxysilane, often used as a hydrophobizing agent in surface treatments, was also very poor when applied alone.

EXAMPLE 14 — Illustrating the Treatment of Aluminum to Render it Water- and Oil-Repellent A solution of 0.02 g destructible fluorocarbylalkoxysilane surfactant-3, 20 g deionized water, and 0.1 g of 1 wt. % aqueous sulfuric acid was prepared by mixing in this order. This was placed in a pump sprayer and sprayed onto coupons of milled aluminum (Alcan 5052-0 Mg-Al alloy mill treated with chromate and cleaned in a 1:1 ethanol/methylene chloride sonic bath) to the point where the entire surface was just completely wet. The coupons were dried and heated in air to 250° C. for 5 minutes. The samples showed outstanding water repellency as measured by a static advancing contact angle of 155–165 degrees which was stable to aging against 18 MOhm water (Millipore, Milli-Q TM). On the same sample the hexadecane (Aldrich, 99%) static contact angle was 53–54 degrees, also stable to aging. By increasing the concentration of surfactant-3 from the 0.1 wt. % described above to 0.5 wt. % by use of 0.1 g of surfactant-3 in a solution prepared as above, spray application and 250° C./5 minutes cure, the hexadecane contact angle was raised to 93 degrees, stable to aging, while the contact angle to 18 MOhm water remained the same. The pathologically high contact angles were a combined result of the milled surface and the pattern of the coating which developed.

EXAMPLE 15 — Illustrating the Use of Destructible Silane Surfactants to Exhaust Emulsions of Water-Insoluble Fluorocarbvlsilanes Onto Wool Fabric to Render it Water- and Oil-Repellent, and Effects of Subsequent Rinsing Into 250 ml screw-top glass jars were added surfactant and $C_8F_{17}SO_2N(Et)(CH_2)_3Si(OMe)_3$ (silane 5, prepared according to the method of Example 6), in the weights and ratios given in TABLE IV designed to yield 0.05 g of hydrolyzed and condensed fluorosilsequioxane product in each example for direct comparison. Each surfactant and its fluorosilane oil were blended together without solvent to achieve a homogeneous solution. To each such solution, 200 g of deionized water (18 Mohm, Millipore Milli-Q TM) was added and a metastable emulsion formed by agitation for 5 minutes on a table shaker. The emulsions were acidified with 3.3 g of 1 wt. % sulfuric acid, reshaken by hand briefly, and single piece 10.0 g samples of 100% wool test fabric added to each in a loose roll. The capped jars were then shaken for four hours at 25° C. at four cycles per second on the table shaker during which time the emulsions cleared. The fabric was removed and dried overnight flat between paper towels at room temperature. Static repellency tests were run (see Tests A and B above), and the results were as summarized in the first Sample History entries in TABLE IV under "dried at ambient". The tested sections were cut away, and the remaining pieces heated to 150° C. for 5 minutes and retested. The results are listed in the second Sample History entries of TABLE IV under "heated 150° C./5 min". To illustrate that fluorosiloxane films formed in each case and that the stable nonionic surfactants FC171 TM (3M Company) and D-683 TM (Tergitol TM D-683 TM, Union Carbide Corp.) give lower repellency due to surfactant contamination, the tested regions of the samples were cut away, and the remaining pieces were rinsed three times by shaking with 200 ml deionized water for one hour each, dried in air, reheated to 150° C. for 5 minutes, and retested. The results are shown in the third Sample History entries in TABLE IV under "1st rinse cycle". The tested portions of the samples were again removed, and the remainders were rinsed thoroughly with three 200 ml portions of deionized water, each rinse shaken on the table shaker at 25° C. at four cycles per second for 24 hours, dried in air, reheated to 150° C. for 5 minutes, and retested. The results are listed in the fourth Sample History entries in TABLE IV under "2nd rinse cycle".

TABLE IV

Static Repellencies After Exhaustion Application of Fluorosilane Emulsions onto Wool, 0.5 wt % SOF[1]

| Surfactant | wt. g | silane 5[2] wt. g | Sample History (see test) | OR | WR |
|---|---|---|---|---|---|
| Surfactant-3 | 0.012 | 0.050 | Dried at ambient | 4(6) | 0(1) |
|  |  |  | Heated 150° C., 5 min | 6(8) | 3(5) |
|  | poor dispersion |  | 1st rinse cycle | 6(7) | 5(7) |
|  |  |  | 2nd rinse cycle | 5(6) | 6(6) |
| Surfactant-3 | 0.022 | 0.041 | Dried at ambient | 7(8) | 1(2) |
|  |  |  | Heated 150° C., 5 min | 6(8) | 4(5) |
|  | fair dispersion |  | 1st rinse cycle | 6(7) | 5(6) |
|  |  |  | 2nd rinse cycle | 5(6) | 6(7) |

TABLE IV-continued

Static Repellencies After
Exhaustion Application of Fluorosilane Emulsions
onto Wool, 0.5 wt % SOF[1]

| Surfactant | silane 5[2] wt. g | wt. g | Sample History (see test) | OR | WR |
|---|---|---|---|---|---|
| surfactant-6 | 0.012 | 0.050 | Dried at ambient | 6(7) | 2(2) |
| | | | Heated 150° C., 5 min | 6(7) | 5(7) |
| good dispersion | | | 1st rinse cycle | 6(7) | 5(7) |
| | | | 2nd rinse cycle | 5(6) | 5(7) |
| Surfactant-6 | 0.021 | 0.042 | Dried at ambient | 6(7) | 2(2) |
| | | | Heated 150° C., 5 min | 5(7) | 5(6) |
| excellent dispersion | | | 1st rinse cycle | 5(7) | 5(6) |
| | | | 2nd rinse cycle | 5(8) | 6(7) |
| D-683[2] | 0.013 | 0.062 | Dried at ambient | 0(0) | 0(1) |
| (comparative) | | | Heated 150° C., 5 min | 0(0) | 1(2) |
| good dispersion | | | 1st rinse cycle | 5(6) | 2(3) |
| | | | 2nd rinse cycle | 5(6) | 3(4) |
| D-683[2] | 0.023 | 0.065 | Dried at ambient | 0(0) | 0(0) |
| (comparative) | | | Heated 150° C., 5 min | 0(1) | 1(1) |
| good dispersion | | | 1st rinse cycle | 0(0) | 2(3) |
| | | | 2nd rinse cycle | 0(0) | 2(3) |
| FC171[2] | 0.013 | 0.066 | Dried at ambient | 6(7) | 1(1) |
| (comparative) | | | Heated 150° C., 5 min | 6(7) | 3(5) |
| good dispersion | | | 1st rinse cycle | 6(7) | 4(6) |
| | | | 2nd rinse cycle | 6(6) | 4(5) |
| FC171[2] | 0.023 | 0.061 | Dried at ambient | 0(0) | 0(0) |
| (comparative) | | | Heated 150° C., 5 min | 6(7) | 1(2) |
| good dispersion | | | 1st rinse cycle | 6(7) | 2(3) |
| | | | 2nd rinse cycle | 6(7) | 3(3) |
| Comparative[3] | 0.021 | 0 | Dried at ambient | 0(0) | 0(1) |
| | | | Heated 150° C., 5 min | 0(0) | 1(1) |
| FC171 only | | | 1st rinse cycle | 0(0) | 2(2) |
| | | | 2nd rinse cycle | 0(0) | 2(2) |
| Comparative[4] | 0 | 0.060 | Heated 150° C., 5 min | 0(0) | 3(3) |
| Comparative[5] | 0 | 0 | Dried at ambient | 0(0) | 2(2) |
| | | | Heated 150° C., 5 min | 0(0) | 2(2) |
| | | | 1st rinse cycle | 0(0) | 2(2) |
| | | | 2nd rinse cycle | 0(0) | 2(2) |

(1) 10.0 g 100% wool test fabric in one piece, 200 g aqueous surfactant stabilized emulsion containing 0.05 g of fluorosilsequioxane equivalent, 3.3 g 1 wt. % sulfuric acid catalyst gave initial pH 3, temperature of exhaustion 25° C., 4 hours exhaustion time at four cycles per second on the table shaker.

(2) Silane was $C_8F_{17}SO_2N(Et)C_3H_6Si(OCH_3)_3$ prepared using the procedure of Example 6, D-683 is Tergitol D-683 nonionic emulsifier available from Union Carbide Corp., $FC_{171}$ is a methoxy-terminated fluorochemical nonionic emulsifier available from 3M Company.

(3) 10.0 g 100% wool test fabric in one piece, 200 g deionized water containing 0.021 g FC171 surfactant and 3.3 g 1 wt. % sulfuric acid to give initial pH 3, temperature of exhaustion 25° C., 4 hours exhaustion time at four cycles per second on the table shaker.

(4) 10.0 g 100% wool test fabric in one piece, 200 g aqueous coarse dispersion of 0.060 g silane 5 without surfactant, 3.3 g 1 wt. % sulfuric acid catalyst to give initial pH 3, temperature of exhaustion 25° C., 18 hours exhaustion time at four cycles per second on the table shaker.

(5) 10.0 g 100% wool test fabric in one piece, 200 g deionized water containing 3.3 g 1 wt. % sulfuric acid catalyst gave initial pH 3, temperature of exhaustion 25° C., 4 hours exhaustion time at four cycles per second on the table shaker.

The room temperature dried coatings showed excellent oil repellency for the good dispersions of silane 5 using the destructible surfactants, increasing with an increase in the level of use of these surfactants. On the other hand, oil repellency at ambient cure was seen for the dispersions using the stable surfactants only at low surfactant concentrations. The water repellency for the destructible surfactant delivered systems was improved to acceptable levels by curing the coating to drive the siloxane condensation to completion while leaving the oil repellency unchanged. The heated films differentiated the fluorinated stable surfactant from the non-fluorinated stable surfactant delivered coatings showing excellent oil repellency for the former but no oil repellency for the latter. The only exceptions to this occurred for lower levels of use of these surfactants, bordering on the edge of gross emulsion instability. While heating improved the water repellency for the films formed using the stable surfactants, these numbers were for the most part two points below those obtained in the totally destructible systems. Rinsing the films with water improved all the water repellencies of the redried films, increasing the WR with increasing extent of washing, with only a little loss of oil repellency. These results demonstrated the detrimental contamination of repellent surfaces when stable surfactants were used to deliver the emulsions. However, in the case of high use levels of D-683, even copious washing was insufficient to remove the contamination.

Thus the advantages of a destructible surfactant in forming repellent coatings are 1) increased ambient cure oil repellency, 2) improved water repellency after heating, 3) less sensitivity of repellency to the level of surfactant used to stabilize the emulsion, 4) decreased need to rinse the films to remove contaminating surfactant, and 5) the absence of a fluorinated surfactant in a waste stream. The positive effects on wetting and penetration of dyes and other treatments into the fabric in the presence of materials yielding low tension in the initial stages is retained by use of such destructible surfactants as described here. A control example with the silane 5 and no surfactant demonstrates the importance of achieving adequate dispersion of the reactive oil, and the role of surfactant in emulsion stabilization required to encourage film formation over deposition of fluorosiloxane particulate.

EXAMPLE 16 —Illustrating the Dynamic Water Repellency of Exhaustion Treated Wool Fabric Using Emulsions of Water-Insoluble Fluorocarbylsilanes as a Function of Exhaustion Time Single 10 g pieces of 100% wool test fabric were treated by exhaustion of silane 5 emulsions, stabilized by surfactants in the weights and ratios given in TABLE V, designed to yield 0.05 g of fluorosiloxane product in each example for direct comparison using the method described in Example 15, and for the times indicated in TABLE V. The samples were removed from the exhaustion liquid, dried flat between paper towels overnight, heated to 150° C. for 5 minutes, tested for static water (WR) and oil (OR) repellency (see Tests A and B, above), the tested portions trimmed away, and the remainder tested in the Bundesman apparatus for dynamic water repellency as absorbed water (Wa) and water throughout (WT) as described in Test C, above. Elemental fluorine analysis (ppm F) was then obtained on a central portion of the redried samples. All these measures are tabulated in TABLE V, below.

tion in this case was the destructible silane surfactant delivered emulsion which had high static water repellency regardless of exhaustion time.

The absorbed water in the samples from the dynamic water wetting tests (Wa) tracked the static repellencies in a linear relationship with slope of $-3$, showing that the destructible systems were as superior in dynamic repellency as they were in static repellency. The methoxy-terminated fluorocarbyl nonionic FC171 is superior to the hydroxyterminated fluorocarbyl nonionic FC170C as expected for the latter's increased hydrophilicity. And both fluorocarbyl surfactants were superior to the comparable hydrocarbyl surfactant delivered coatings in this measure. The water passed measure (WT) in general decreased exponentially with increasing static water repellency. Again the destructible system yielded the lowest number and therefore the best performance.

While the charged silane in each case was designed to yield 2800 ppm fluorine on the fabric, it is apparent that in most cases less fluorosilane was actually transferred. The destructible system was most efficient in capturing the charged fluorine in a layer on the fabric. Some of the low levels, for example the D-683 stabilized emulsions, may have been due to the formation of fluorosilane particulate as observed by scanning electron microscopy, with the particulate not being easily combusted in the analysis and not contributing to repellency. Again, there was a clear advantage to the use of destructible surfactants in these applications.

TABLE V

Static and Dynamic Repellencies After Exhaustion Application of Fluorosilane 5 Emulsions onto Wool, 0.5 wt % SOF[a]

| Sample | Surfactant wt gm | Silane 5[b] wt gm | Exh. time hrs | OR | WR | Wa wt % | WT ml | F[c] ppm |
|---|---|---|---|---|---|---|---|---|
| Surfactant-6 | 0.013 | 0.057 | 4 | 6(7) | 6(6) | 25 | 4 | 2826 |
|  |  |  | 18 | 6(7) | 6(7) | 26 | 2 | 3421 |
| FC170C[b] | 0.013 | 0.066 | 4 | 6(7) | 4(6) | 36 | 13 | 1567 |
|  |  |  | 18 | 6(8) | 5(7) | 33 | 34 | 2088 |
| FC171[b] | 0.013 | 0.066 | 4 | 6(7) | 4(5) | 30 | 6 | 1768 |
|  |  |  | 18 | 6(7) | 5(8) | 28 | 9 | 1906 |
| D-683[b] | 0.024 | 0.067 | 4 | 0(1) | 2(2) | 40 | 18 | 739 |
|  |  |  | 18 | 6(8) | 3(6) | 36 | 26 | 2899 |
| D-683[b] | 0.008 | 0.063 | 4 | 6(7) | 3(4) | 35 | 10 | 864 |
|  |  |  | 18 | 6(8) | 4(6) | 30 | 19 | 2705 |
| Comparative FC171 only | 0.013 | — | 4 | 0(0) | 1(1) | 47 | 180 | 142 |
|  |  |  | 18 | 0(0) | 1(1) | 45 | 163 | 22 |
| Comparative (untreated fabric) | — | — | 4 | 0(0) | 6(6) | 45 | 144 | 74 |
|  |  |  | 18 | 0(0) | 2(2) | 45 | 100 | 59 |

[a]See Note 1, TABLE IV. Variable time of exhaustion
[b]See Note 2, TABLE IV. FC170C is a hydroxy-terminated fluorocarbyl polyethylene oxide nonionic surfactant available from 3M Company
[c]Fluorine elemental analysis performed by combustion With the sole exception of the hydrocarbyl nonionic emulsifier D-683 at high levels, the static oil repellencies were invariant with choice of surfactant in this group or time of exhaustion. The D-683 delivered coating of the product from silane 5 hydrolysis and condensation improved markedly with longer exhaustion time, similar to the results obtained with rinsing (see Example 15) and perhaps for the same reason, i.e., equilibration of the trapped hydrocarbyl surfactant (detrimental to hydrocarbon oil repellency) back into the aqueous exhaustion phase. Larger differences occurred with the static water repellencies, showing two to three point improvements when using fluorochemical emulsifiers over hydrocarbon emulsifiers and in both cases, and further improvement with longer exhaustion time. The excep- EXAMPLE 17 —Illustrating the Effect of Fluorochemical Group Structure on Repellency of Fluorosilane Exhaustion Treated Wool Average structures of the fluorinated alkoxysilanes used in this Example appear in TABLE VI.

Into 250 ml screw-top glass jars were added the destructible fluorosilane surfactants in the weights listed in TABLE VI designed to yield 2800 ppm fluorine in each for comparison to data in Examples 12, 15, and 16. To each was added 200 ml deionized water and solutions formed by shaking for 5 minutes on the table shaker (4 cps). The solutions ranged from clear to very cloudy depending on the cloud point of each material. They were acidified to pH 3 by addition of 3 ml of 1 wt. % sulfuric acid, briefly reshaken, and 10.7 g of 100% wool test fabric added in one piece to each. The bottles were capped and placed back on the table shaker for 18 hours at 25° C. and at four cycles per second agitation. The fabric pieces were removed from the exhaustion liquid, dried flat between paper towels, and then heated to 150° C. for 5 minutes to complete the siloxane cure. The samples were then tested for static oil (OR) and water (WR) repellency by the methods outlined in Tests A and B, above. The results are summarized in TABLE VI.

fluoroalkyl as in surfactant-13 showed improved oil but unchanged water repellency in the siloxane layer it generates when compared to that formed from surfactant-12 having an n-alkyl chain with the same number of fluorine atoms. Thus chain length may have had more of an effect when penetration of larger alkanes was at issue than for the smaller water molecules. The reproducible high water repellency of the pentadecylfluoroheptyl carboxamide was at variance with this explanation, however. It may have been that for a suffi-

TABLE VI

Static Repellencies After Exhaustion Application of Various Distructible Fluorosilane Surfactants of Varied Number of $CF_2$ Groups onto 10.7 gm Wool, 2800 ppm F[1]

| Surfactant No. | MW gm/mole | wt. gm | OR | WR |
|---|---|---|---|---|
| surfactant-3 $C_8F_{17}SO_2N(Et)C_3H_6Si(OC_2H_5)_{0.53}O(C_2H_4O)_3CH_3)_{2.47}$ | 1086 | 0.108 | 6(7) | 5(6) |
| surfactant-10 $C_4F_9SO_2N(Et)C_3H_6Si(OCH_3)_{0.61}(O(C_2H_4O)_3CH_3)_{2.39}$ [3] | 886 | 0.160 | 3(5) | 3(4) |
| surfactant-11 $C_7F_{15}CONHC_3H_6Si(OCH_3)_{0.16}(O(C_2H_4O)_3)_{2.84}$ [4] | 972 | 0.101 | 5(6) | 9(10) |
| surfactant-12 $C_5F_{15}CONHC_3H_6Si(OCH_3)_{0.37}(O(C_2H_4O)_3CH_3)_{2.63}$ [5] | 872 | 0.130 | 3(3) | 3(3) |
| surfactant-13 $C_2F_5OC_2F_4OCF_2CONHC_3H_6Si(OCH_3)_{0.44}(OC_2H_5)_{0.1}(O(C_2H_4O)_2CH_3)_{2.46}$ [6] | 772 | 0.120 | 6(6) | 3(4) |
| 8 $CF_3C_2H_4Si(OC_2H_4OCH_3)_3$ [7] (comparative) | 350 | 0.184 | 0(0) | 1(1) |
| comparative (untreated fabric) | — | — | 0(0) | 1(2) |

(1) Exhaustion bath concentrations of fluorosilanes adjusted to give approximately the same 2800 ppm fluorine charged in each (2) OR and WR are static repellencies determined as described in Tests A and B in the text (3) Surfactant-10 was obtained from treatment of $C_4F_9SO_2N(Et)CH_2CH=CH_2$ with trichlorosilane and Pt/divinyltetramethyldisiloxane as catalyst, followed by conversion to the trimethoxysilane by methanolysis in methanol/triethylamine, followed by treatment with triethylene glycol monomethyl ether according to the procedure described in Example 3

(4) Surfactant-11 was obtained from treatment of $C_7F_{15}CO_2CH_3$ (available from PCR) with 3-aminopropyltrimethoxysilane, then treatment of the product with triethylene glycol monomethyl ether according to the procedure described in Example 4

(5) Surfactant-12 was obtained from treatment of $C_5F_{11}CO_2CH_3$ with 3-aminopropyltrimethoxysilane, then treatment of the resulting product with triethylene glycol monomethyl ether as described in Example 4

(6) Surfactant-13 was obtained from treatment of $C_2F_5OC_2F_4OCF_2CO_2CH_2CH_3$ with 3-aminopropyltrimethoxysilane, then treatment of the resulting product with diethylene glycol monomethyl ether using the procedure described in Example 4

(7) Silane 8 was obtained from treatment of $CF_3C_2H_4SiCl_3$ (Hüls) with 2-methoxyethanol (Aldrich) and triethylamine according to the procedure in Example 1

These data show that the onset of useful repellency in condensed fluorosiloxane layers on wool occurred at or near ($R_f$=n-nonafluorobutyl when B=$SO_2N(Et)C_3H_6$ and at or near $R_f$=n-undecafluoropentyl when B=$CONHC_3H_6$. The need for a slightly longer chain of fluorochemical was understandable when comparing the N-alkyl structure of the former to the more polar and acidic NH structure of the latter. Five fluorinated carbons when arrayed as a seven atom dioxaperciently long fluoroalkyl group, the intermolecular hydrogen bonding of the CONH segment led to a particularly high degree of ordering of the condensed fluorosiloxane repellent layer, driving out water, as this function is known to prefer hydrogen bonding to itself rather than water. Examples of this type of behavior are well known in protein and aminoplast chemistries. The prior art trifluoromethyl group-containing silane s was seen to be totally ineffective in either generating a condensed layer or displaying fluoroalkane in such a layer even when the least polar connecting group possible (B=$C_2H_4$) is used.

EXAMPLE 18 —Illustrating the Ineffectiveness of Trifluoroorooovl Siloxane Layers as per U.S. Pat. No. 4,865,910 to Generate Repellent Surfaces on Wool at Any Reasonable Level of Use (Comparative)

Into 250 ml screw-top jars were added weights of silane 9, $CF_3C_2H_4Si(O(C_2H_4O)_2CH_3)_3$, prepared according to the procedure of Example 1 using $CF_3C_2H_4SiCl_3$ from Petrarch Chemical Co., as specified in TABLE VII. To each was added 200 ml deionized water and the surfactant dissolved. To the first sample in TABLE VII, dilute sulfuric acid was added to yield a pH of 2. In the second and fourth samples, the pH was adjusted to 4 using dilute sulfuric acid. In the third sample, no acid was added and a native pH of 6 was measured using a calibrated Metrohm meter and glass combination electrode. The acid addition was followed immediately by immersion of 10.8 gm samples of 100% wool test fabric in single pieces, the jars capped, and the exhaustions allowed to proceed for 18 hours at 25° C. and at four cycles per second on the table shaker. The fabric was removed from the exhaustion liquid, dried flat between paper towels overnight, and then heated to 150° C. for five minutes. The pH of the recovered exhaustion liquids were measured and the results are recorded in TABLE VII. Static oil and water repellency tests were run as described in Tests A and B, above. These results are also recorded in TABLE VII. After trimming away the tested portions, Bundesman dynamic water tests were performed on the remaining samples as described in Test C, above. The water absorbed (Wa) and the water passed through the samples (WT) are recorded in TABLE VII. After redrying the samples, fluorine elemental analyses were run by combustion. These results are also recorded in TABLE VII as ppm F.

TABLE VII
(comparative)
Static and Dynamic Repellencies of 10.8 gm samples of 100% Wool Treated by Exhaustion with Silane 9 at Various Levels and pH

| Silane 13 wt. gm | pH initial | pH final | OR | WR | Wa wt % | WT ml | F ppm |
|---|---|---|---|---|---|---|---|
| 0.195 | 2 | 4 | 0(0) | 1(2) | 54 | 181 | 125 |
| 0.210 | 4 | 6 | 0(0) | 1(2) | 45 | 122 | 223 |
| 0.204 | 6 | 7 | 0(0) | 1(1) | 45 | 158 | 95 |
| 2.101 | 4 | 7 | 0(0) | 1(2) | 44 | 87 | 4156 |
| 0 | 4 | 7 | 0(0) | 2(2) | 45 | 163 | 64 |

Although elemental analysis showed above background levels of fluorine incorporation in most of these samples, no static or significant dynamic repellency was seen for any of these treatments. The low level of fluorine incorporation and poor dynamic water repellency of the pH 2 example was due to the reversibility of the siloxane condensation. This was demonstrated in concentrated aqueous solutions of silane 9 where after precipitation of the siloxane at pH 4, the solid could be totally redissolved upon lowering the pH to 2. This fact, more severe for this siloxane than any others described in this document, also may explain the in general low levels of fluorine on the fabric seen here even at higher pH. The conclusion here is that the trifluoropropyl group-bearing silanes taught by U.S. Pat. No. 4,865,910 for glass fiber treatments in composites are totally inappropriate for generation of oil-and water-repellent fabric finishes.

Various modifications and alterations of this invention will become apparent to those skilled in the art without departing from the scope and spirit of this invention, and it should be understood that this invention is not to be unduly limited to the illustrative embodiments set forth herein.

We claim:

1. A fluorocarbylalkoxysilane surfactant comprising a hydrophilic portion and a hydrophobic portion, said surfactant comprising at least one polyfluorinated aliphatic or polyfluorinated ether group and at least one hydrophilic polyol, polyol ether, or polyoxyalkylene group, said fluorocarbylalkoxysilane being destructible by hydrolysis.

2. The fluorocarbylalkoxysilane according to claim 1 wherein said hydrophilic polyol, polyol ether, or polyoxyalkylene group can be completely or partially cleaved from said hydrophobic portion of said surfactant by hydrolysis and completely or partially condensed to a siloxane.

3. The fluorocarbylalkoxysilane according to claim 1 having a cloud point at a temperature in the range of 0 to 100° C. when 1 weight percent of said fluorocarbylalkoxysilane is admixed with water.

4. The fluorocarbylalkoxysilane according to claim 1 comprising at least one of the formulae:

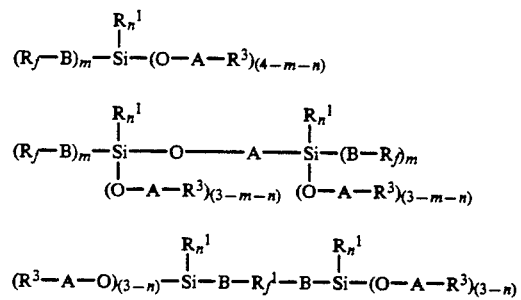

wherein: each A is independently 1) a covalent bond, or 2) a divalent hydrophilic group (a) having the formula $(CHR^2-CH_2O)_q$ in which q is a number having a value of 1 to 40, preferably 2 to 10, $R^2$ is hydrogen or methyl, and that at least 70% of $R^2$ is hydrogen, or (b) derived from a polyol or its alkyl ether or polyether derivative by removal of one OH and one hydroxyl hydrogen;

B is a divalent organic connecting group joining Si to $R_f$ or $R_f^1$ that is substantially stable against hydrolysis;

$R_f$ is a monovalent polyfluoroaliphatic group having at least 2 carbon atoms and at least 30 weight percent fluorine;

$R_f^1$ is a divalent polyfluoroaliphatic group having at least 6 carbon atoms and at least 30 weight percent of fluorine;

$R^1$ is an alkyl group having 1 to 18 carbon atoms or phenyl;

$R^2$ is hydrogen, or methyl, no more than 30% of $R^2$ being methyl;

$R^3$ is independently hydrogen or lower alkyl group having 1 to 4 carbon atoms;

m independently is an integer having a value of 1, 2, or 3;

n independently is zero or an integer having a value of 1 or 2;

m+n has a sum total value of 1, 2, or 3; with the provisos that at least one of A is a divalent hydrophilic group as previously disclosed and that the balance of $R_f$ or $R_f^1$ groups to said hydrophilic groups is such that a one percent by Weight mixture of the surfactant in water has a cloud point in the range of 0° C. to 100° C.

5. The fluorocarbylalkoxysilane according to claim 4 wherein B comprises a divalent connecting group selected from the group consisting of an arylene group,

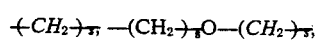

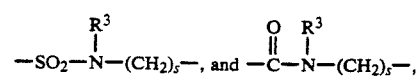

in which $R^3$ is as defined above, and each s and s' independently are integers in the range of 1 to 12.

6. The fluorocarbylalkoxysilane according to claim 4 wherein $R_f$—B is selected from the group consisting of

C₈F₁₇SO₂NCH₂CH₂CH₂—,
      |
      CH₂CH₃

C₈F₁₇SO₂NCH₂CH₂CH₂—,
      |
      CH₃

C₈F₁₇CH₂CH₂—, and

C₇F₁₅CONHCH₂CH₂CH₂.

7. The fluorocarbylalkoxysilane according to claim 4 wherein R_f is selected from the group consisting of (1) a monovalent straight chain or branched polyfluoroaliphatic group having 2 to 24 carbon atoms, cyclic polyfluoroaliphatic group having 4 to 24 carbon atoms, optionally containing chlorine atoms, or oxygen bonded only to carbon atoms, provided that not more than one atom of either of hydrogen or chlorine is present for every two carbon atoms, or (2) a monovalent polyfluoroalkoxy poly(fluorooxyalkylene) group having a number average molecular weight of 250 to 2,000.

8. The fluorocarbylalkoxysilane according to claim 4 wherein $R_f^1$ is selected from the group consisting of (1) a divalent straight chain, branched chain, or cyclic polyfluoroaliphatic group having 6 to 24 carbon atoms, optionally containing chlorine atoms, or optionally containing oxygen bonded only to carbon atoms, provided that no more than one atom of either hydrogen or chlorine is present for every two carbon atoms, or (2) a divalent poly(fluorooxyalkylene) group having a number average molecular weight of 300 to 2,000.

9. A composition of matter comprising the fluorocarbylsilane and its partial hydrolysis and condensation products according to claim 2 and water.

10. The composition according to claim 9 further comprising at least one hydrocarbylalkoxysilane or halocarbylalkoxysilane having an alkyl or haloalkyl group of 1 to 24 carbon atoms and at least one $C_1$ to $C_4$ alkoxy group.

11. The composition according to claim 10 wherein said hydrocarbylalkoxysilane or halocarbylalkoxysilane has the formula $$R_f^6 Si(OR^5)_{4-t} \qquad \text{IX}$$

in which $R^5$ is a lower alkyl group of $C_1$ to $C_4$, t is an integer having a value of 0, 1, 2, or 3, and $R^6$ is $R_f$—B as defined above or a monovalent group selected from alkyl groups having 1 to 24 carbon atoms, aryl, alkaryl, and aralkyl groups having 6 to 12 carbon atoms, wherein none or up to 25 percent of hydrogen atoms may be substituted by fluorine or chlorine atoms in the alkyl and aryl groups.

12. The composition according to claim 10 wherein said hydrocarbylalkoxysilane is selected from the group consisting of methyltriethoxysilane, dimethyldiethoxysilane, butyltriethoxysilane, octyltrimethoxysilane, dodecyltriethoxysilane, octadecyltriethoxysilane, phenyltriethoxysilane, the corresponding chlorosubstituted alkylalkoxysilanes, and tetraethoxysilane.

13. The composition according to claim 12 wherein said halocarbylalkoxysilane is selected from the group consisting of chloromethyltriethoxysilane, chlorobutyltriethoxysilane, 3-(2,2,2-trifluoroethoxy)propyltriethoxysilane, 3-(N-ethylperfluorooctylsulfonamido)propyltrimethoxysilane, 3-(perfluorooctylamido)propyltrimethoxysilane, and 3-(perfluoroheptylmethoxy)propyltriethoxysilane.

14. The composition according to claim 9 further comprising an effective amount of a catalyst for hydrolysis and condensation reaction.

15. The composition according to claim 9 which is useful in oil- and water-repellent applications.

16. The cured composition according to claim 2.

17. The cured composition according to claim 9.

18. An article comprising a substrate comprising a layer of the composition according to claim 16.

19. An article comprising a substrate comprising a layer of the composition according to claim 9.

20. A method for preparing an article having oil and water repellant properties comprising the steps:
  1) providing an aqueous composition of destructible nonionic surfactant according to claim 1 as described above;
  2) coating the substrate with a layer of the composition of step 1 or immersing the substrate into the composition of step 1 for a time sufficient to form an adsorbed layer of the composition on at least a portion of the substrate;
  3) drying the coating; and
  4) curing the coating.

21. The method according to claim 20 wherein said substrate is selected from the group consisting of a textile, glass, ceramic, metal, concrete, and masonry.

22. The method according to claim 21 wherein said textile is selected from the group consisting of cotton, polyester, acrylic, nylon, polyolefin, wool, and combinations of the foregoing.

23. A method for preparing a destructible fluorinated alkoxysiloxane surfactant according to claim 1 comprising the steps of
  reacting a polyoxyalkylene alcohol with a polyfluoroaliphatic halosilane, a polyfluoroaliphatic alkoxysilane, a polyfluoroaliphatic bis(alkoxysilane) or a polyfluoroaliphatic bis(halosilane), to provide a destructible surfactant.

24. The method according to claim 20 further comprising the step of hydrolyzing said destructible surfactant in the presence of a substrate so as to provide a water- and oil-repellent coating on said substrate or to provide oil- and water-repellent particles.

* * * * *

UNITED STATES PATENT AND TRADEMARK OFFICE
CERTIFICATE OF CORRECTION

PATENT NO. 5,274,159

DATED December 28, 1993

INVENTOR(S) Mark J. Pellerite et al.

It is certified that error appears in the above-indentified patent and that said Letters Patent is hereby corrected as shown below:

Col. 5, line 45, replace "HO-A-A$^3$IV" with -- HO-A-R$^3$ IV --.

Col. 5, line 58, "of I to 4" should read -- of 1 to 4 --.

Col. 6, line 10, "form" should read -- from --.

Col. 6, line 54, "Rf" should read -- R$_f$ --.

Col. 8, line 16, "H s America, Inc." should read -- Hüls America, Inc. --.

Col. 8, line 21, "R$_f$SO$_2$NMR$^3$" should read -- R$_f$SO$_2$NHR$^3$ --.

Col. 8, line 50, "is Formula IX or" should read -- in Formula IX is --.

Col. 8, line 62, "6 to I2" should read -- 6 to 12 --.

Col. 9, line 52, "I0 seconds" should read -- 10 seconds --.

Col. 10, line 30, "677.064:620 193.2" should read -- 677.064:620.193.2 --.

Col. 10, line 30, "of I40" should read -- of 140 --.

Col. 11, line 2, "75 ml Of" should read -- 75 ml of --.

UNITED STATES PATENT AND TRADEMARK OFFICE
CERTIFICATE OF CORRECTION

PATENT NO. : 5,274,159

DATED : December 28, 1993

INVENTOR(S) : Mark J. Pellerite et al.

It is certified that error appears in the above-indentified patent and that said Letters Patent is hereby corrected as shown below:

Col. 11, line 25, "$C_7F_{15}CH_2O(CH_2)_3Si[O(CH_2CH_2O)_3CH_3[_3$" should read -- $C_7F_{15}CH_2O(CH_2)_3Si[O(CH_2CH_2O)_3CH_3]_3$ --.

Col. 11, line 47, "$C_8F_{17}SO_2N(Et)(CH_2)_3Si(OPEt)_3(2)$" should read -- $C_8F_{17}SO_2N(Et)(CH_2)_3Si(OEt)_3(2)$ --.

Col. 13, line 3, "Formula 111" should be -- Formula III --.

Col. 13, line 30, "$-CONH(C_3H_6)Si(OMe)_x(O(C_2H_4O)_3CH_3)Y$" should read -- $-CONH(C_3H_6)Si(OMe)_x(O(C_2H_4O)_3CH_3)_y$ --.

Col. 13, line 37, "about minutes" should read -- about 30 minutes --.

Col. 13, line 43, "(by volume) Mohm" should read -- (by volume) 18 Mohm --.

Col. 13, line 55, "to be dyn/cm" should read -- to be 66 dyn/cm --.

Col. 13, line 58, "(Surfactant-S)" should read -- (surfactant-8) --.

Col. 13, lines 60-61, "$X-CF_2O(CF_2)_a(C_2F_4O)_bCF_2-X$" should read -- $X-CF_2O(CF_2O)_a(C_2F_4O)_bCF_2-X$ --.

Col. 13, line 65, "0H equivalent" should read -- OH equivalent --.

UNITED STATES PATENT AND TRADEMARK OFFICE
CERTIFICATE OF CORRECTION

PATENT NO. : 5,274,159

DATED : December 28, 1993

INVENTOR(S) : Mark J. Pellerite et al.

It is certified that error appears in the above-indentified patent and that said Letters Patent is hereby corrected as shown below:

Col. 14, line 31, "With an" should read -- with an --.

Col. 15, in Table I, the third column's heading should read -- Solution age -- instead of "Solution Dye --.

Col. 16, line 51, "$C_{18},H_{37}$" should read -- $C_{18}H_{37}$ --.

Col. 16, line 51, "below-as " should read -- below as --.

Col. 18, line 7, "Fluorocarbvsilanes" should read -- fluorocarbylsilanes --.

Col. 19, Table IV, in the second entry for "surfactant-6", Heated 150°C, 5 min (OR) should be 6(7); first rinse cycle (OR) should be 6(7) --.

Col. 19, line 45, "$FC_{171}$" should read -- FC171 --.

Col. 21, Table V, for the first Comparative Sample, the entry under the "$F^{(c)}$ppm" column should be -- 222 -- instead of "22"; and for the second Comparative Sample, the entry under the "WR" column should be -- 2(2) -- instead of "6(6)".

Col. 23, Table VI, in the second line of the title of the Table, "Distructible" should be -- Destructible --.

UNITED STATES PATENT AND TRADEMARK OFFICE
CERTIFICATE OF CORRECTION

PATENT NO. : 5,274,159

DATED : December 28, 1993

INVENTOR(S) : Mark J. Pellerite et al.

It is certified that error appears in the above-indentified patent and that said Letters Patent is hereby corrected as shown below:

Col. 23, Table VI, in the entry for surfactant-12, the chemical formula should be
-- $C_5F_{11}CONHC_3H_6Si(OCH_3)_{0.37}(O(C_2H_4O)_3CH_3)_{2.63}(5)$ --.

Col. 24, line 37, "silane s" should be -- silane 8 --.

Col. 24, line 44, "Trifluorooroovl" should read -- trifluoropropyl --.

Col. 24, line 48, "$CF_3C_2H_4Si(0(C_2H_4O)_2CH_3)_3$" should read -- $CF_3C_2H_4Si(O(C_2H_4O)_2CH_3)_3$ --.

Col. 25, line 67, "claim I" should be -- claim 1 --.

Col. 26, line 40, "having I to 4" should be -- having 1 to 4 --.

Col. 26, line 49, "by Weight" should be -- by weight --.

UNITED STATES PATENT AND TRADEMARK OFFICE
CERTIFICATE OF CORRECTION

PATENT NO. : 5,274,159
DATED : December 28, 1993
INVENTOR(S) : Mark J. Pellerite, et al It is certified that error appears in the above-indentified patent and that said Letters Patent is hereby corrected as shown below:

Col. 26, line 56, the formulae should read -- $-(CH_2)-_s$, $-(CH_2)-_s-O-(CH_2)-_{s'}-$, Signed and Sealed this Sixteenth Day of August, 1994

Attest:

BRUCE LEHMAN

Attesting Officer    Commissioner of Patents and Trademarks